United States Patent [19]

Chung et al.

[11] Patent Number: 5,039,546

[45] Date of Patent: Aug. 13, 1991

[54] FLUORIDE TREATMENT OF HYDROXYAPATITE COATED METAL IMPLANTS

[76] Inventors: Harvey Chung, 29632 Island View Dr., Rancho Palos Verdes, Calif. 90274; Sung-Tsuen Liu, 29 Landing, Laguna Niguel, Calif. 92677

[21] Appl. No.: 475,282

[22] Filed: Feb. 5, 1990

[51] Int. Cl.$^5$ ............................................. B05D 3/10
[52] U.S. Cl. ..................................... 427/2; 427/343; 427/430.1; 427/443.2
[58] Field of Search ............. 427/343, 2, 430.1, 443.2

[56] References Cited

U.S. PATENT DOCUMENTS

| | | | |
|---|---|---|---|
| 4,687,675 | 8/1987 | Nakano | 427/2 |
| 4,746,532 | 5/1988 | Suzuki et al. | 427/2 |
| 4,795,475 | 1/1989 | Walker | 427/2 |
| 4,801,300 | 1/1989 | Kurze et al. | 427/2 |
| 4,847,163 | 7/1989 | Shimamune et al. | 427/2 |
| 4,871,578 | 10/1989 | Adam et al. | 427/2 |

*Primary Examiner*—Janyce Bell
*Attorney, Agent, or Firm*—Irving Keschner

[57] ABSTRACT

A method for decreasing the dissolution rate of a hydroxyapatite coating or other calcium phosphate coating formed on a metal substrate by treating the coated metal substrate in a fluoride ion containing solution. The effective reagents for fluoride treatment can be any solution which supplies fluoride ion with the suitable pH of the solution being 3 or higher, preferably 5 or higher. The treatment enhances the stability of the coating strength.

8 Claims, No Drawings

FLUORIDE TREATMENT OF HYDROXYAPATITE COATED METAL IMPLANTS

BACKGROUND OF THE INVENTION

1. Field of the Invention

The present invention relates to a method for increasing the stability of hydroxyapatite coatings, or other calcium phosphate coatings, on metal implants. The coated metal substrates have important applications in dental and orthopaedic areas as implant materials.

2. Description of the Prior Art

Hydroxyapatite and tricalcium phosphate ceramics have been used as hard tissue replacement materials particularly in the dental areas for many years. The major inorganic component of human bones and teeth is biological apatite. Because of the similarity in chemical composition and crystal structure between hydroxyapatite ceramic and biological apatite, hydroxyapatite ceramic has excellent biocompatibility in comparison with other implant materials such as metals and plastics. Besides the excellent biocompatibility, hydroxyapatite ceramic also has conductive effect for bone growth and can bond very strongly with bone. Most of the clinical studies indicate that dense hydroxyapatite ceramics are not bioresorbable while other calcium phosphate ceramics are bioresorbable.

Currently, a coating of hydroxyapatite on metal substrates has expanded the medical applications of hydroxyapatite ceramic considerably. The coating of hydroxyapatite on the surface of metal implants provides excellent biocompatibility and can bond tightly with bone. The healing time of hydroxyapatite coated metal implants is much shorter than the un-coated metal implants. Currently, the hydroxyapatite coated metal implants have been used in the orthopaedic and dental areas. Many coating techniques can be utilized to coat hydroxyapatite or other calcium phosphate containing material on metal substrates. These include plasma flame coating, ion sputtering coating and high temperature compressing and sintering. At the present time, plasma flame spraying seems to be the most feasible technique for hydroxyapatite coating. However, due to the high temperature involved, the plasma flame coated hydroxyapatite is not pure hydroxyapatite. It always contains some decomposed products such as calcium oxide, amorphous hydroxyapatite, tricalcium phosphate and tetracalcium phosphate. The degree of decomposition depends strongly on the raw material used and the coating parameters. The coating of ceramics by the plasma flame method typically ends up with a porous structure. The decomposed products of hydroxyapatite normally have higher solubility values and dissolve readily in comparison with pure hydroxyapatite. Due to the decomposed products and the porous nature of hydroxyapatite by the plasma flame spraying technique, the bonding strength between the ceramics and metal substrate deteriorates in an aqueous environment such as the body fluid condition. Similar deterioration in coating bonding strength occurs for other calcium phosphate coatings. This raises concerns on the long term stability of the plasma flame coated hydroxyapatite or other calcium phosphate material. On the other hand, the ion sputtering coating can produce very dense coating. However, the coating thickness is very thin and most of the hydroxyapatite coating is either amphorous phase or un-identified calcium phosphates. This coating can be completely dissolved before bone growth.

A prior art technique discloses the post-treatment of plasma flame coated hydroxyapatite by removing the decomposed product, calcium oxide, to improve the biocompatibility of the plasma flame coated hydroxyapatite. By using special reagents the decomposed product calcium oxide is bleached out, the major calcium phosphate ceramic not being affected. However, this treatment does not improve the dissolution resistance of the coating nor reduce the deterioration rate of the coating strength of the hydroxyapatite coating in an aqueous environment.

What is thus desired is to provide a technique for decreasing the dissolution rate of the hydroxyapatite coating or other calcium phosphate based coating material on a metal substrate and to enhance the stability of the coatings in an aqueous environment.

SUMMARY OF THE INVENTION

The present invention provides a method of treatment to decrease the dissolution rate of the hydroxyapatite coating or other calcium phosphate based ceramic coating formed on a metal substrate and to enhance the stability of the coating strength by soaking the hydroxyapatite or calcium phosphate ceramic coated metal substrates in a fluoride ion containing solution, thus making the substrate particularly useful as hard tissue implant materials, such as dental and hip joint implants.

The fluoride treatment can be applied to the coated metal substrates utilizing conventional techniques. For example, plasma flame, ion sputtering and compressing sintering coating techniques could be utilized. The effective reagents for fluoride treatment can be any solution which supplies the fluoride ion. Among these solutions are lithium fluoride, cesium fluoride, sodium fluoride, potassium fluoride, ammonium fluoride, acidulated phosphate fluoride, stannous fluoride, and any other solution which provides the fluoride ion, such as sodium hexafluorosilicate and sodium fluorophosphate. The pH of the solution for fluoride treatment should be 3 or higher, preferably 5 or higher. The hydroxyapatite coated substrates coated in accordance with the teachings of the present invention are not limited to pure hydroxyapatite coatings, but also can contain other impurities such as amorphous hydroxyapatite, calcium oxide and decomposed calcium phosphate. For example, the final coating of hydroxyapatite by plasma flame spraying always contains undecomposed hydroxyapatite, amorphous hydroxyapatite, calcium oxide and calcium phosphate. After fluoride treatment, this ceramic coating converts to very insoluble fluorapatite and other insoluble fluoride compounds, the coating thus becoming more resistant to dissolution in an aqueous environment.

The effective reagents for fluoride treatment can be any solution which supplies the fluoride ion. Among these solutions are lithium fluoride, cesium fluoride, sodium fluoride, potassium fluoride, ammonium fluoride, acidulated phosphate fluoride, stannous fluoride and any other solution which provides the fluoride ion. The pH of the solution for fluoride treatment should be 3 or higher, preferably 5 or higher.

DETAILED DESCRIPTION OF THE INVENTION

According to the teachings of the present invention, a metal substrate having a hydroxyapatite (HA) ceramic coating formed thereon by one of the aforementioned coating techniques is treated in a fluoride ion containing solution for a predetermined time period. The treated sample is then washed and rinsed with pure water and then dried. After fluoride treatment, this HA coating on the metal substrate was found to have a reduced dissolution rate which in turn enhanced the stability of the HA coating strength, an important feature since the HA coated metal substrate used as implant material is subjected to the liquid environment of the body, such as in the oral cavity.

In an example illustrating the benefits of the present invention, plasma flame coated HA dental implants from both Core Vent Company, Encino, Calif. and Calcitek Incorporated, Carlsbad, Calif., were used for treatment. The Core Vent dental implants were cylindrical in form with a 3.5 mm diameter and 8 mm length; the Calcitek implants were also cylindrical in form with a 4 mm diameter and 8 mm length. The dental implants were made from titanium alloy and the outside surfaces were coated with HA by the plasma flame spraying technique.

A solution of ammonium fluoride was prepared by dissolving ammonium fluoride salt in pure water to make a 2% ammonium fluoride solution. The temperature of the fluoride ion containing solution is in the range from about 1° C. to its boiling point, the temperature only affecting the treatment reaction rate. The preferable concentration of the fluoride ion in the solution ranges from about 0.001% to about 5%. Twenty (20) ml of ammonium fluoride solution was then added to a vial in a sufficient amount to immerse the treated coated metal substrate. Each dental implant was then soaked in a separate vial containing the same amount of ammonium fluoride solution for approximately 12 hours. The time period of immersion is dependent upon the solution fluoride ion concentration and the solution temperature. The dental implant was then washed and rinsed with deionized water, and then air dried. It should be noted that other solvents, such as alcohol or acetone, could be used to wash the implant.

To ascertain the change in dissolution rates, a 0.5% acetic acid solution was used. For comparison purposes, fluoride treated and non-treated samples were used. Each dental implant was introduced into a vial containing 15 ml 0.5% acetic acid solution. After thirty minutes, the dental implant was removed, and the solution was saved for calcium analysis for the dissolved calcium phosphate salt. The acid soaked dental implant samples as well as the original non-acid soaked samples were used for scanning electron microscopic observation. The dissolved calcium ion in acid dissolution study was determined by the atomic absorption method. The following is the result of the dissolution study.

| SAMPLE | TREATMENT | DISSOLVED CALCIUM ION CONCENTRATION (MG/L) |
|---|---|---|
| Core Vent | no treatment | 150 |
| Core Vent | fluoride treatment | 8.5 |
| Core Vent | fluoride treatment* | 8.5 |
| Calcitek | no treatment | 96 |
| Calcitek | fluoride treatment | 9.4 |

*(This sample was heated to 600° C. for a half hour before fluoride treatment.)

It is clear that the fluoride treatment of the HA coated dental implant decreases the dissolution rate considerably. After fluoride treatment, the undecomposed HA together with the decomposed products such as oxyapatite, tricalcium phosphate and tetracalcium phosphate will convert to less soluble fluoride compounds such as fluorapatite and calcium fluoride. The decreased dissolution rate of the HA coating by fluoride treatment therefore enhances the stability of the HA coating considerably in the liquid environment within the body.

The process of the present invention, as noted above, is particularly useful to treat HA ceramic or other calcium phosphate ceramic coated metal substrates, although the invention can be used with other coatings, such as tricalcium phosphate, tetracalcium phosphate or other calcium phosphate ceramic coatings and mixtures thereof, such as mixtures of calcium phosphate and HA with noncalcium phosphate ceramics, metals or alloys.

The scanning electron microscopic observation also indicated that the fluoride treated samples are more resistant to dissolution than the un-treated samples. For example, the fluoride treated samples after acid soaking retained the integrity of the coating and showed similar surface morphology of the coating as the original sample without acid soaking. On the other hand, those samples without fluoride treatment showed considerable surface damage and morphology change of the coating after acid soaking. It also appeared that the fluoride treated samples after acid soaking were more resistant to scratching like the original samples in comparison with the un-treated samples after acid soaking.

The present invention thus provides a simple and cost effective technique for enhancing the stability of the HA coating on metal implants, thus increasing the effective life of the implant which in turn minimizes the discomfort, treatment times and costs to the implant recipient.

While the invention has been described with reference to its preferred embodiment, it will be understood by those skilled in the art that various changes may be made and equivalents may be substituted for elements thereof without departing from the true spirit and scope of the invention. In addition, many modifications may be made to adapt a particular situation or material to the teaching of the invention without departing from its essential teachings.

What is claimed is:

1. A method for improving the stability of the coating strength and decreasing the biodegradation rate of a calcium phosphate based material coating formed on a metal substrate comprising the step of immersing the metal substrate in a fluoride ion containing solution for a time period necessary to convert the metal substrate coating to one containing less soluble fluoride compounds.

2. The method of claim 1 wherein said fluoride ion containing solution is selected from the group consisting of lithium fluoride, cesium fluoride, sodium fluoride, potassium fluoride, ammonium fluoride and stannous fluoride.

3. The method of claim 2 wherein said fluoride ion containing solution has a pH value greater than 3.

4. The method of claim 2 wherein the fluoride ion containing solution has a pH value of 5 or higher.

5. The method of claim 1 wherein the concentration of the fluoride ion in the fluoride ion containing solution ranges from 0.001% to 5%.

6. The method of claim 1 where said coating comprises hydroxyapatite.

7. The method of claim 1 further including the steps of washing the substrate after immersion and thereafter drying the substrate.

8. The method of claim 1 wherein said coating comprises apatites.

* * * * *